United States Patent [19]

Suzukamo et al.

[11] 4,312,717

[45] Jan. 26, 1982

[54] PROCESS FOR PRODUCING 2-(2'-METHYL-1'-PROPENYL)-4-METHYL-TETRAHYDROPYRAN

[75] Inventors: Gohu Suzukamo, Ibaraki; Tetsuo Takano, Takatsuki; Mitsuhisa Tamura, Ibaraki; Kiyoshi Ikimi, Kyoto, all of Japan

[73] Assignee: Sumitomo Chemical Company, Limited, Osaka, Japan

[21] Appl. No.: 158,810

[22] Filed: Jun. 12, 1980

[30] Foreign Application Priority Data

Jun. 19, 1979 [JP] Japan .................................. 54-77919
Jun. 20, 1979 [JP] Japan .................................. 54-78602

[51] Int. Cl.$^3$ ............................................. C25B 3/02
[52] U.S. Cl. ................................ 204/59 R; 204/72; 204/79; 204/80
[58] Field of Search .................. 204/59 R, 72, 78, 79, 204/80

[56] References Cited

U.S. PATENT DOCUMENTS 3,390,066 6/1968 Baizer et al. ........................... 204/72

OTHER PUBLICATIONS

Eschinasi, J. Org. Chem., vol. 35 pp. 1097–1100.
Shond et al., Tetrahedron Letter, vol. 39, pp. 3599–3602 (1971).
Hanson et al., J.C.S. Chem. Comm. 1975, pp. 271, 272.
Ohloff et al., Helvetica Chimica Acta, vol. 48, pp. 182–189 (1965).
Hidai et al., Oil Chem. Soc. vol. 25, pp. 549–552 (1976).
Furukawa et al., Tetrahedron, vol. 29, pp. 3149–3151 (1973).

*Primary Examiner*—F. Edmundson
*Attorney, Agent, or Firm*—Cushman, Darby & Cushman

[57] ABSTRACT

Rose oxide, which is an important olfactive compound valuable in the art of perfumery, is advantageously produced from citronellol through a novel synthetic route comprising (1) anodic alkoxylation of citronellol using as a supporting electrolyte an alkali metal aromatic sulfonate,
(2) dealkoxylation of the resulting 2,6-dimethyl-3-alkoxyoct-1-en-8-ol in the presence of a palladium or nickel complex, and then
(3) cyclization of the resulting dehydrocitronellol in the presence of an acid.

8 Claims, No Drawings

PROCESS FOR PRODUCING 2-(2'-METHYL-1'-PROPENYL)-4-METHYLTETRAHYDROPYRAN

The present invention relates to a novel process for producing rose oxide which is a monoterpene oxide, namely, 2-(2'-methyl-1'-propenyl)-4-methyltetrahydropyran.

More specifically, the present invention relates to a process for producing optically active or racemic rose oxide using as the starting material optically active or racemic citronellol through a novel synthetic route.

Rose oxide is an important olfactive compound valuable in the art of perfumery, and in order to produce the same industrially advantageously from citronellol, many attempts have been made, for example, as described below;

(1) a process for the production of the same through the preparation of citronellyl acetate and then dehydrocitronellyl acetate, as disclosed in French Pat. No. 1,539,054, and J. Org. Chem. 35, 1097 (1970), (2) a process for the production thereof through the preparation of citronellol epoxide, as disclosed in Dutch Patent Application No. 6,503,936, or Helv. Chim. Acta. 48, 182 (1965), (3) a process for the production thereof through the preparation of dehydrocitronellol, as disclosed in Dutch Patent Application No. 6,903,287, and (4) a process for the production of the same directly by electrolysis, as disclosed in Japanese published examined patent application No. 27511/1972.

However, these processes cannot be said to be advantageous from industrial point of view, because of drawbacks such that a dangerous peroxide must be used in an equimolar amount, a high temperature reaction is required, or the yield of rose oxide is generally unsatisfactory.

Under these circumstances, the present inventors have earnestly studied to find an industrially advantageous process for the production of rose oxide using citronellol as the starting material, and as a result, found that a high purity rose oxide can be produced industrially advantageously through the following novel synthetic route;

First step (anodic methoxylation)

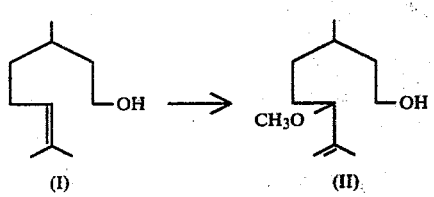

Second step (dealkoxylation)

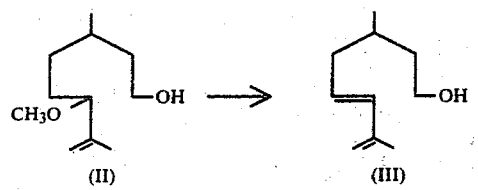

Third step (cyclization)

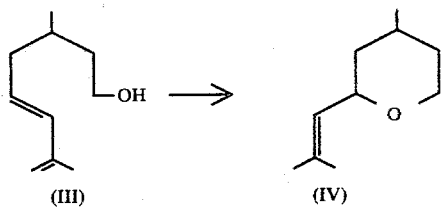

As for the production of 2,6-dimethyl-3-methoxyoct-1-en-8-ol (II) by anodic methoxylation of citronellol (I), there is disclosed in Tetrahedron Letters, (1971) 3599, a process comprising electrolysis of citronellol (I) in methanol using a tetraalkylammonium p-toluenesulfonate as a supporting electrolyte. This process is, however, unsatisfactory from industrial point of view, because of low yield of the 2,6-dimethyl-3-methoxyoct-1-en-8-ol (II) and use of the tetraalkylammonium p-toluenesulfonate which is difficult in handling and expensive.

As for the production of 2,6-dimethyl-1,3-octadien-8-ol (III) (hereinafter referred to as dehydrocitronellol) by dealkoxylation of the 2,6-dimethyl-3-methoxyoct-1-en-8-ol (II), many attempts have heretofore been proposed to synthesize an olefin by dealkoxylation of an ether using as a catalyst, for example, (1) an organic base as disclosed in J. Am. Chem. Soc. 73, 5708 (1951) or Chem. Lett. (1975) 1167, and (2) an acid or acidic substance as disclosed in Chem Ber., 100, 1764 (1967) of Synthesis, (1976) 545. These catalysts are, however, unsatisfactory for dealkoxylation of the 2,6-dimethyl-3-methoxyoct-1-en-8-ol to produce the dehydrocitronellol in high yields.

Thus, an object of the present invention is to provide a process for producing 2,6-dimethyl-3-alkoxyoct-1-en-8-ol by anodic alkoxylation of citronellol in high yields.

Another object of the present invention is to provide a process for producing dehydrocitronellol by alkoxylation of the 2,6-dimethyl-3-alkoxyoct-1-en-8-ol in high yields.

Further object of the present invention is to provide a process for producing rose oxide through a novel synthetic route with industrial advantages.

These and other objects of the present invention can be accomplished by providing (1) a process for producing 2,6-dimethyl-3-alkoxyoct-1-en-8-ol, which comprises anodic alkoxylation of citronellol in an alcohol in the presence of an alkali metal aromatic sulfonate as a supporting electrolyte, (2) a process for producing dehydrocitronellol by dealkoxylation of 2,6-dimethyl-3-alkoxyoct-1-en-8-ol in the presence of a palladium or nickel complex, and (3) a process for producing rose oxide, which comprises the steps (i) anodic alkoxylation of citronellol in an alcohol in the presence of an alkali metal aromatic sulfonate as a supporting electrolyte to obtain (2,6-dimethyl-3-alkoxyoct-1-en-8-ol, (ii) dealkoxylation of the resulting 2,6-dimethyl-3-methoxyoct-1-en-8-ol in the presence of a palladium or nickel complex and a base to obtain dehydrocitronellol, and (iii) cyclization of the resulting dehydrocitronellol to obtain rose oxide in the presence of an acid.

The processes of the present invention will be explained in detail as follows.

Anodic alkoxylation of citronellol

The alcohol usable in the present invention serves as a reaction solvent (electrolytic solution) and a reactant, and includes lower alcohols having 1 to 3 carbon atoms. Of these, the particularly preferred is methanol.

As the supporting electrolytes, there can be employed different kinds of alkali metal aromatic sulfonate generally known by the person skilled in the art. The particularly preferred are those which have benzene nucleus unsubstituted or substituted with a lower alkyl group as the aromatic group, and sodium or potassium as the alkali metal. Preferred examples are sodium or potassium benzenesulfonate, sodium or potassium p-toluenesulfonate, sodium or potassium naphthalenesulfonate and the like.

The concentration of the supporting electrolyte in the electrolytic solution ranges preferably from 0.5 to 10% by weight, more preferably from 1 to 3% by weight.

The concentration of the starting material, citronellol, in the electrolytic solution is not particularly limited. Too low concentration is uneconomical, whereas too high concentration readily results in low yields of the desired compound. Suitable concentration thereof ranges from 5 to 60% by weight, preferably from 10 to 40% by weight. When an optically active citronellol is used as the starting material, an optically active desired compound can be obtained.

As for electrodes usable in carrying out the electrolysis in accordance with the present invention, the anodes are made of carbon, platinum or the like, preferably carbon, and the cathodes are made of carbon, graphite, platinum, aluminum, silver, copper, steel or other metals or alloys.

As the electrolytic bath usable in the present invention, there may be an electrolytic bath undivided or divided by a diaphragm.

In carrying out the electrolysis using such electrolytic bath, it is preferable to keep the electrode potential ranging from 2 to 10 volt and the current density ranging from 0.5 to 20 A/dm$^2$. The temperature of the electrolytic solution is not particularly limited as far as it is not higher than the boiling point of the alcohol used. The preferred lower limit is 40° C. In order to perform the electrolysis efficiently, it is desirable to stir the anode solution vigorously, for example, by means of stirring by a usual stirrer or high speed circulation by a pump.

The unreacted citronellol, the supporting electrolyte and the alcohol can be separated and recovered by distillation, extraction or other conventional means, and then reused for the electrolysis.

Dealkoxylation of the 2,6-dimethyl-3-alkoxyoct-1-en-8-ol

The 2,6-dimethyl-3-alkoxyoct-1-en-8-ol obtained by the above anodic alkoxylation is converted into dehydrocitronellol by dealkoxylation reaction in an alcohol solvent in the presence of a palladium or nickel complex and a base.

As a main catalyst, there is used a palladium complex of the formula, PdL$_2$X$_2$, or a nickel complex of the formula, NiL'$_2$, wherein L is a trialkylphosphine ligand, L' is a cyclic diene ligand, and X is a halogen atom.

Among the palladium complex catalysts, the preferred are those which have a straight alkyl groups of 1 to 12 carbon atoms as the alkyl group in the trialkylphosphine L and a chlorine atom as the halogen atom X. Preferred examples include bis(tri-n-butylphosphine) palladium (II) chloride, bis(tri-n-octylphosphine)palladium (II) chloride and the like. The palladium complex catalyst prepared in advance may be used for the dealkoxylation reaction, or a palladium (II) halide and a trialkylphosphine may be separately added into the reaction system.

Among the nickel complex catalysts, the preferred are those having an eight-membered ring as the cyclic diene. Bis(cyclooctadiene) nickel (0) is exemplified as a preferred catalyst. In employing the nickel complex, it is preferred to use a straight trialkylphosphine having 1 to 12 carbon atoms at the same time in an amount of 4 or more moles per mole of the complex, whereby the catalytic efficiency can be increased markedly. Tri-n-butylphosphine is particularly preferred as the trialkylphosphine.

The base to be used together with the above main catalyst, the palladium or nickel complex, includes various kinds of organometallic reducing compounds. Of these, organosodium and organolithium compounds are preferred. Particularly preferable examples are sodium methoxide, n-butyllithium and the like. The amount thereof is from 2 to 6 moles per mole of the palladium or nickel complex. Less than 2 moles are insufficient for exhibiting the catalytic activity, while more than 6 moles cannot be expected to increase the effect.

The solvent usable for the dealkoxylation reaction in accordance with the present invention includes lower alcohols having 1 to 4 carbon atoms, or a mixture thereof. Examples of particularly effective solvents include methanol, ethanol, isopropanol, a methanol-isopropanol mixture and the like. The mixing ratio in the mixtue is 1:5 to 5:1, preferably about 1:1.

The concentration of the 2,6-dimethyl-3-alkoxyoct-1-en-8-ol in the alcohol ranges from 0.5 to 40% by weight, preferably from 1 to 20% by weight.

The palladium or nickel complex is used in an amount of 0.1 to 10% by mole based on the mole of the 2,6-dimethyl-3-alkoxyoct-1-en-8-ol. Taking into consideration of the reaction rate and the cost of the catalyst, the ranges from 0.5 to 2.5% by mole are preferable from industrial point of view.

The reaction temperature ranges from 50° to 120° C., preferably from 60° to 100° C. Temperatures lower than 50° C. take a long period of time for completion of the reaction, while temperatures higher than 120° C. are not preferable because of decreasing the yield of the desired compound.

The reaction time varies depending upon the reaction conditions. Under the conditions as described above for the catalyst concentrations and temperature ranges, it is within 12 hours.

In order to increase the yield of the desired compound, it is preferable to carry out the dealkoxylation reaction in an atmosphere of an inert gas such as dry argon, nitrogen and the like.

The reaction mixture is subjected to removal of the catalyst and then purification by distillation, thereby obtaining the desired dehydrocitronellol.

Cyclization of dehydrocitronellol

The dehydrocitronellol obtained by the above dealkoxylation reaction is converted into rose oxide by cyclization in the presence of an acid catalyst. The cyclization of the dehydrocitronellol can easily be carried out using an acid catalyst such as sulfuric acid, p-toluenesulfonic acid and the like in a manner known per se, for example, as disclosed in J. Org. Chem. 35, 1097 (1970). The acid catalyst is used in an amount of 0.1 to 30% by mole based on the mole of the dehydrocitronellol. As the acid catalyst, inorganic acids and organic acids can be used. The best result can be attained by use of sulfuric acid in an amount of 20 to 60% by weight based on the weight of the dehydrocitronellol.

A suitable amount of water is used as the reaction solvent, but additional water need not be used when a diluted acid (an aqueous acid solution) is used as the catalyst.

The reaction temperature is preferably from 20° to 100° C., more preferably from 30° to 60° C.

The reaction time is, in general, within 10 hours.

The desired rose oxide can be obtained in high purity by rectification of the reaction mixture.

In accordance with the process of the present invention, an optically active rose oxide can be obtained using as the starting material an optically active citronellol.

The present invention is explained in more detail with reference to the following Examples, which are only illustrative and not intended to limit the scope of the present invention.

The identification and determination of the products were made by IR, NMR, gas chromatography and mass spectroscopy, and the yield of each reaction product was calculated by the following formula, $$\frac{\text{Mole number of the product}}{\text{Mole number of the starting compound}} \times 100\ (\%)$$

EXAMPLE 1

Two carbon rods of 10 mm in diameter and 30 mm in length as electrodes were placed in a 30 cc glass vessel, and the distance between the electrodes was fixed at 2 mm. In this electrolytic bath were added 11 g of methanol, 1.2 g of citronellol and 0.2 g of sodium benzenesulfonate. Thereafter, the electrolysis was carried out at room temperature under a nitrogen atmosphere at a constant current of 0.25 A, and continued until the electricity reached 3.0 Faraday/mole. During the electrolysis, the electrode potential was kept at 4 to 5 volt.

The results of analysis for the reaction product were as follows:

| | |
|---|---|
| Conversion of citronellol | 94.6% |
| Yield of 2,6-dimethyl-3-methoxyoct-1-en-8-ol (containing a small amount of isomer thereof) | 56.4% |
| Yield of 2,6-dimethyl-2,3-dimethoxyoctanol-8 | 9.5% |
| Yield of rose oxide | 2.7% |

EXAMPLES 2 to 4

Using the supporting electrolyte as shown in Table 1, the reaction was carried out in the same manner as in Example 1. In Example 4, however, the reaction temperature was 60° C.

The results are as shown in Table 1.

TABLE 1

| Exp. No. | Supporting electrolyte | Faraday/mole of citronellol | Conversion of citronellol (%) | Yield of 2,6-dimethyl-3-methoxyoct-1-en-8-ol* (%) | Yield of 2,6-dimethyl-2,3-dimethoxyoctanol-8 (%) | Yield of rose oxide (%) |
|---|---|---|---|---|---|---|
| 2 | CH$_3$—⌬—SO$_3$Na | 2.5 | 89.7 | 50.2 | 10.0 | 2.0 |
| 3 | naphthyl-SO$_3$Na | 2.5 | 69.4 | 34.3 | 6.2 | 1.6 |
| 4 | ⌬—SO$_3$Na | 2.5 | 86.3 | 56.0 | 11.4 | 3.4 |

*A small amount of isomers was contained.

EXAMPLE 5

Example 1 was repeated, provided that ethanol was used in place of methanol and the reaction temperature was 60° C. The electrode potential was kept at 7 to 8 volt.

The results were as shown below:

| | |
|---|---|
| Conversion of citronellol | 84.9% |
| Yield of 2,6-dimethyl-3-ethoxyoct-en-8-ol (containing a small amount of isomers thereof) | 44.3% |
| Yield of rose oxide | 2.0% |

COMPARATIVE EXAMPLE 1

Example 1 was repeated, provided that 0.3 g (1 mmole) of tetraethylammonium p-toluenesulfonate was used as the supporting electrolyte.

The results were as shown below:

| | |
|---|---|
| Conversion of citronellol | 96.4% |
| Yield of 2,6-dimethyl-3-methoxyoct-1-en-8-ol (containing a small amount of isomers thereof) | 33.5% |
| Yield of 2,6-dimethyl-2,3-dimethoxyoctanol-8 | 8.3% |
| Yield of rose oxide | 4.0% |

EXAMPLE 6

Example 1 was repeated, and the resulting electrolysis reaction mixture was subjected to distillation to remove methanol. Thereafter, the residue was rectified under reduced pressure of 2 mmHg, and the fraction from 105° to 107° C. was collected to obtain 2,6-dimethyl-3-methoxyoct-1-en-8-ol.

EXAMPLE 7

In 10 cc of purified ethanol was dissolved 1.0 mmol of 2,6-dimethyl-3-methoxyoct-1-en-8-ol, and the resulting solution was introduced into a well dried 50 cc three-necked flask equipped with a reflux condenser and a septum cap, using a hypodermic syringe under a nitrogen atmosphere. Successively, 0.05 mmol of bis(tri-n-butylophosphine)palladium (II) chloride and 0.15 mmol of sodium methoxide were added thereto in this order. Thereafter, the mixture was heated to 80° to 85° C., and the reaction was continued for 5 hours at that temperature under stirring with a magnetic stirrer.

The results of analysis for the reaction mixture were as shown below:

| | |
|---|---|
| Conversion of 2,6-dimethyl-3-methoxyoct-1-en-8-ol | 92.0% |
| Yield of dehydrocitronellol | 81.4% |

EXAMPLE 8

In a manner similar to that of Example 7, the reaction was carried out, provided that 0.1 mmole of bis(tri-n-octylphosphine)palladium (II) chloride was used as the catalyst. The results were as follows:

| | |
|---|---|
| Conversion of 2,6-dimethyl-3-methoxyoct-1-en-8-ol | 86.5% |
| Yield of dehydrocitronellol | 67.3% |

EXAMPLE 9

In a manner similar to that of Example 7, the reaction was carried out, provided that 0.1 mmole of palladium (II) chloride, 0.2 mmole of tri-n-butylphosphine and 0.3 mmole of sodium methoxide was separately added to the reaction system as the catalyst. The results were as follows:

| | |
|---|---|
| Conversion of 2,6-dimethyl-3-methoxyoct-1-en-8-ol | 83.5% |
| Yield of dehydrocitronellol | 66.9% |

EXAMPLE 10

In a manner similar to that of Example 7, the reaction was carried out, provided that 0.1 mmole of bis(cyclooctadiene)nickel (0) and 0.3 mmole of sodium methoxide as the catalyst, and 0.4 mmole of tri-n-butylphosphine as the additive were used. The results were as follows:

| | |
|---|---|
| Conversion of 2,6-dimethyl-3-methoxyoct-1-en-8-ol | 54.5% |
| Yield of dehydrocitronellol | 32.9% |

EXAMPLE 11

In a manner similar to that of Example 7, the reaction was carried out, provided that 0.1 mmole of bis(tri-n-butylphosphine)palladium (II) chloride as the catalyst, and 0.3 mmole of butyllithium were used. The results were as follows:

| | |
|---|---|
| Conversion of 2,6-dimethyl-3-methoxyoct-1-en-8-ol | 100% |
| Yield of dehydrocitronellol | 58.4% |

EXAMPLE 12

The demethoxylation reaction mixture obtained in Example 7 was washed with water and then extracted with ether. The extract was concentrated to obtain 8 g of dehydrocitronellol. In a 30 cc flask equipped with a condenser at the upper part were placed whole of the dehydrocitronellol obtained and 5 ml of 30% sulfuric acid. Thereafter, the reaction was continued for 2.5 hours at 60° C. under vigorous stirring with a magnetic stirrer. The results of gas chromatographic analysis for the reaction mixture were as follows:

| | |
|---|---|
| Conversion of dehydrocitronellol | 98.9% |
| Yield of rose oxide | 98.5% |

The cis/trans ratio was about 90/10.

EXAMPLE 13

Using 15 g of an optically active citronellol ($[\alpha]_D^{20} - 4.14°$ neat), each reaction was carried out in the same manners as in Examples 6, 7 and 12, whereby 5.3 g of an optically active rose oxide ($[\alpha]_D^{20} - 34.8°$ neat) was obtained. The cis/trans ratio was about 95/5.

We claim:

1. A process for producing 2,6-dimethyl-3-alkoxyoct-1-en-8-ol, which comprises anodic alkoxylation of citronellol in an alcohol in the presence of an alkali metal benzene or toluene sulfonate as a supporting electrolyte.

2. The process according to claim 1, wherein the alcohol is methanol.

3. The process according to claim 1, wherein the anodic alkoxylation is carried out at a temperature of 40° C. or higher.

4. The process according to claim 1, wherein the supporting electrolyte is sodium or potassium benzenesulfonate or sodium or potassium p-toluenesulfonate.

5. The process according to claim 1, wherein the concentration of the supporting electrolyte in the alcohol is from 0.5 to 10% by weight.

6. The process according to claim 1, wherein the concentration of citronellol in the alcohol is from 5 to 60% by weight.

7. The process according to claim 1, wherein the anodic alkoxylation is carried out at an electrode potential of 2 to 10 volt and a current density of 0.5 to 20 $A/dm^2$.

8. The process of claim 1 wherein the supporting electrolyte is sodium benzenesulfonate or sodium p-toluenesulfonate.

* * * * *